United States Patent
Dal Farra et al.

(10) Patent No.: US 8,722,108 B2
(45) Date of Patent: May 13, 2014

(54) COSMETIC AND/OR PHARMACEUTICAL COMPOSITION COMPRISING AN EXTRACT OF CAROB AS ACTIVE AGENT FOR ACTIVATING AQUAPORIN EXPRESSION

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/518,388

(22) PCT Filed: Dec. 21, 2010

(86) PCT No.: PCT/FR2010/000855
§ 371 (c)(1),
(2), (4) Date: Jun. 21, 2012

(87) PCT Pub. No.: WO2011/077017
PCT Pub. Date: Jun. 30, 2011

(65) Prior Publication Data
US 2012/0282198 A1   Nov. 8, 2012

(30) Foreign Application Priority Data
Dec. 24, 2009 (FR) ...................................... 09 06346

(51) Int. Cl.
*A61K 36/00* (2006.01)

(52) U.S. Cl.
USPC ........................................................ 424/725

(58) Field of Classification Search
None
See application file for complete search history.

(56) References Cited

U.S. PATENT DOCUMENTS

2011/0052514 A1 *  3/2011  Justen et al. .................... 424/59

FOREIGN PATENT DOCUMENTS

| EP | 0237398 | 9/1987 |
| FR | 2934779 | 2/2010 |
| FR | 2934779 A1 * | 2/2010 |
| WO | 2009/101503 | 8/2009 |

OTHER PUBLICATIONS

Parrado et al., Bioresource Technology, 99 (2008) 2312-2318.*
http://www.plant-hormones.info/gibberellinhistory.htm (accessed on Dec. 23, 2013).

* cited by examiner

*Primary Examiner* — Michael G Hartley
*Assistant Examiner* — Robert Cabral
(74) *Attorney, Agent, or Firm* — Thompson Hine L.L.P.

(57) ABSTRACT

The invention relates to a cosmetic and/or pharmaceutical composition comprising, in a physiologically suitable medium, a carob peptide extract (*Ceratonia siliqua* L.) as an active agent for promoting aquaporin expression. The present invention also relates to the use of a carob peptide extract (*Ceratonia siliqua* L.), as an active agent for promoting aquaporin expression, in a cosmetic composition for improving the moisturization and the barrier function of the epidermis and for stimulating skin regeneration. The invention also relates to the use of this novel active agent for preparing a pharmaceutical, in particular dermatological, composition for regulating and/or stimulating aquaporin activity. The invention also relates to a cosmetic treatment method for preventing or combating dryness of the skin and mucous membranes and the manifestations of skin aging.

5 Claims, No Drawings

COSMETIC AND/OR PHARMACEUTICAL COMPOSITION COMPRISING AN EXTRACT OF CAROB AS ACTIVE AGENT FOR ACTIVATING AQUAPORIN EXPRESSION

CROSS REFERENCE TO RELATED APPLICATIONS

This application is the national stage of PCT Application No. PCT/FR2010/000855 filed Dec. 21, 2010, which claims priority from French Patent Application No. 0906346, filed Dec. 24, 2009, the entire disclosures of which are hereby incorporated in their entirety.

FIELD OF THE INVENTION

The present invention pertains to the cosmetic and pharmaceutical fields, in particular to the field of dermatology. The invention relates to a cosmetic and/or pharmaceutical composition comprising, in a physiologically suitable medium, a peptide extract of carob (*Ceratonia siliqua* L.) as an active agent for promoting aquaporin expression, containing peptides having a molecular weight of less than 5 kDa and having a polyphenol content of less than 1%. The present invention also relates to the use of a peptide extract of carob (*Ceratonia siliqua* L.) as an active agent for promoting aquaporin expression in a cosmetic composition for improving hydration and the barrier function of the epidermis and for stimulating skin regeneration. The active agent may be used alone or in combination with other active agents. The invention also relates to the use of such a new active agent for the production of a pharmaceutical, in particular dermatological, composition, administered orally or topically, for combatting and/or stimulating the aquaporin activity, and thus treating pathological conditions involving dryness of the skin or mucous membranes, such as xerosis or eczema, and the symptoms of dry mouth and dryness of the eye. The invention further relates to a cosmetic treatment method intended to prevent or combat dryness of the skin and mucous membranes and manifestations of skin aging, which comprises applying the carob extract to promote aquaporin expression or a composition containing the same on the areas to be treated.

BACKGROUND OF THE INVENTION

The skin is a vital organ composed of several layers (dermis, proliferative layers and stratum corneum) covering the entire surface of the body and essentially providing a barrier function with respect to the external environment. This barrier function relies especially on the quality of the epidermis which, in particular, depends on the stratum corneum's condition and on the balance between the proliferation and differentiation of the epidermal keratinocytes. The quality and appropriate functioning of the skin are closely related to the water content in the different layers of the epidermis. Thus, in normal epidermis, the proliferative layers contain about 70% water, whereas the stratum corneum contains only 10 to 15%.

Hydration of the stratum corneum is the result of three factors: the supply of water from the dermis, water loss to the outside environment, and the ability of the stratum corneum to bind water molecules.

The regulation of water distribution is carried out by hormones (aldosterone, sex hormones), pH or osmotic changes. Cell membranes are by nature hydrophobic and are therefore not highly permeable to water, although water channels exist, which are sorts of pores that facilitate the passage of water and certain solutes.

Aquaporins are a class of transmembrane proteins transporting water and small molecules in solution, such as glycerol and urea, which facilitate water transport in the epithelia and endothelia.

The key function of aquaporins in the epithelia involved in the transport of water or solutes, such as in the kidney, has been extensively studied (Deen et al., 1994). Similarly, aquaporins were rapidly identified in the saliva- or tear-producing exocrine glands. However, the discovery of type 3 aquaporin, or AQP3, in human skin, specifically in the plasma membrane of keratinocytes of the proliferative layers of the epidermis (SOUGRAT R. et al., J. Invest. Dermatol., 2002), highlighted the importance of a regulated flow of water into the skin. AQP3s can transport water and glycerol, with the latter playing an important role both in the formation of the surface hydrolipid film and in the preservation of the stratum corneum's flexibility and sensory qualities.

The importance of AQP3s has been demonstrated in mice. Indeed, the inactivation of the F gene causes multiple skin deficiencies, such as low moisture level, ineffective barrier function, increased tissue regeneration time and reduced elasticity (T. Ma et al., J. Mol. Biol., 2002). It has since been discovered that aquaporin 3 is expressed in dermal fibroblasts where it is involved in the migration of these cells during wound regeneration (Cao C. et al., Biochem J., 2006). On the other hand, aquaporins take part in the barrier function by positively regulating the establishment of cellular bonds and communications of the tight-junction type (Kawedia J. et al., PNAS 104(9), 2007).

AQP3 hydration and content in keratinocytes are closely linked. Thus, the increase in skin AQP3 improves hydration of the epidermis (M. Dumas, J. Drugs Dermatol., June, 2007).

Cutaneous water loss may have several origins, namely hereditary, acquired or related to the environment. In a very dry environment, water loss through evaporation from the stratum corneum is significant and may exceed the rate of replacement through transcellular diffusion.

During skin aging, the skin becomes dry. Thus, in elderly patients, in particular in those aged 50 and above, xerosis or dry mucous membranes associated with lower sebum secretion, hormonal changes or slowdowns of the water flow through the epidermis are often seen to occur. The skin is then subject to itching and tautness, two characteristic symptoms of dry skin. Examples of acquired conditions resulting in dry skin include photo-chemotherapy-induced xerosis and eczema. Examples of acquired diseases causing dry mouth, or xerostomia, include Sjogren's syndrome or neck radiation therapy. Lastly, examples of conditions involving mucosal dryness include vaginal or ocular dryness.

A first alternative treatment for dry skin is to administer topical products intended to restore the skin barrier, such as wetting agents capable of binding water, examples of which include urea and lactic acid entering in the composition of NMF (Natural Moisturizer Factor; proteolytic derivatives of filaggrin), film-forming agents for retaining water, or agents capable of rebuilding the skin barrier (squalene, ceramides, fatty acids,). However, these products have a superficial action which does not correct the biological defects of skin subjected to chronic dehydration.

In this context, as a result of their special properties, aquaporins are potential biological targets for improving skin hydration and reducing signs of skin dryness. Thus, patent FR 2 801 504 describes the increase of AQP3 in the skin by using an extract of *Ajuga turkestanica* plants and has resulted in improved skin hydration. A pomegranate extract has also been reported as an oral or topical active agent to stimulate aquaporin activity and regulate water and glycerol transport in tissues (FR 2 874 502). A total extract of carob pulp, at the same time containing proteins, carbohydrates and polyphenols and its use to moisturize the skin, has been described in French Patent 2 905 857, without the mechanism of action of such an extract being suggested.

On the other hand, a carob bean protein extract obtained through hydrolysis and intended for the production of a fertilizer easily assimilated by plants has already been disclosed (J. Parrado et al., Bioresource Technology 99, 2008). The disclosed extract is rich in low molecular weight peptides, but also sugars and phytohormones. However, phytohormones are polyphenolic compounds that modulate plant growth, but are considered as endocrine disruptors in humans because they are often likely to affect functions such as growth, development, behavior or production. The presence of such compounds is not desirable in an extract intended for a cosmetic or pharmaceutical application.

The present invention relates to a carob bean peptide extract containing peptides having a molecular weight of less than 5 kDa and having a very low polyphenol content (less than 1%) and a sugar content of less than 15%. This chemical composition provides the extract with a high degree of safety and results in a more targeted molecular activity. The inventors have thus found that the extract of the invention promotes the expression of aquaporins, in particular aquaporin 3.

DISCLOSURE OF THE INVENTION

A first object of the present invention is to provide a peptide extract of carob (Ceratonia siliqua L.), as a promoter of aquaporin expression, characterized in that the peptide compounds are peptides having a molecular weight of less than 5 kDa and in that its polyphenol content is less than 1%.

The inventors have indeed found that such a peptide extract of carob, when applied to the skin, improves the hydration and bather function of the epidermis and mucous membranes and stimulates skin regeneration. These properties have been demonstrated by a protection of the skin tissue and a decreased apoptosis in response to water stress.

By "active agent capable of preventing and controlling dryness of the skin and mucous membranes and manifestations of skin aging" is meant any substance capable of improving the hydration and barrier function of the epidermis and mucous membranes or reducing apoptosis in cells or tissues subjected to water stress.

By "peptide extract" is meant a diluted mixture of compounds mainly represented by peptides, dissolved in a large volume of water or other polar solvents, or a mixture of such solvents.

By "topical application" is meant the action of applying or spreading the active agent of the invention or a composition containing the same, onto the surface of the skin or mucous membrane.

By "physiologically acceptable", is meant that the active agent of the invention or a composition containing the same, is suitable for contact with the skin or mucous membranes without causing toxic reactions or intolerance.

By "biologically active" is meant "having in vivo or in vitro activity which is characteristic of the active agent of the invention".

By "peptide compounds" is meant fragments of proteins and peptides present in the peptide extract of the invention.

The characteristic biological activity according to the invention is defined in vitro by the ability of the active agent to activate aquaporin expression, either by increasing the protein synthesis of aquaporin (by direct or indirect modulation of the gene expression of aquaporin), or through other biological processes such as the stabilization of the aquaporin protein or the stabilization of messenger RNA transcripts.

Preferably, according to the present invention, the aquaporin is aquaporin 3, or AQP3, present in the membranes of keratinocytes.

The active agent according to the present invention can be obtained by extracting proteins of plant origin, followed by a controlled hydrolysis, which releases the biologically active peptide compounds.

The use of peptide extracts, in particular peptide extracts of low molecular weight, has many advantages in cosmetics. In addition to generating peptide compounds that did not previously exist in the starting protein mixture, hydrolysis and purification make it possible to obtain mixtures that are more stable, easier to standardize and do not cause allergic reactions in the dermato-cosmetic field.

Numerous proteins of plant origin may contain bioactive peptides within their structure. Mild hydrolysis allows such peptide compounds to be released. It is possible, although not necessary in order to practice the invention, to either first extract, and then hydrolyze the proteins concerned, or to first carry out hydrolysis on a crude extract and then purify the peptide compounds.

To perform extraction, carob seeds are used (plant of the genus *Ceratonia*). Carob is grown in Mediterranean countries and the endosperm fraction of its seeds is used in the food industry under the name "locust bean gum." The germ is the richest part of the seed protein and can be isolated easily.

Any extraction or purification method known to one skilled in the art can be used to prepare the extract of the invention.

In a first step, the germs contained in the seeds are crushed to obtain a powder or flour. The powder thus obtained can be previously treated with a cellulase to promote sugar removal, in particular insoluble polysaccharides.

The proteins are then extracted from the germ according to the conventional modified method (Osborne, 1924); the carob seed homogenate is suspended in an alkaline solution containing an insoluble adsorbent of the polyvinyl polypyrrolidone type (PVPP) (0.01-20%); it has indeed been observed that this facilitated the subsequent hydrolysis and purification steps. In particular, the concentration of phenolic substances, interacting with the proteins, is significantly reduced. The proteins can then be precipitated by varying the ionic strength or by acidifying the medium, which eliminates soluble components and nucleic acids. The precipitate is then washed with an organic solvent such as, for example, ethanol or methanol, and the solvent is then evaporated by vacuum drying. The protein-rich precipitate is redissolved in water or another solvent in order to obtain a more purified form of the extract.

The extraction can also be performed in a neutral or acidic medium again in the presence of polyvinyl polypyrrolidone. After a filtration step, the precipitation step is then carried out using a conventional precipitation agent such as salts (sodium chloride, ammonium sulfate) or an organic solvent (alcohol, acetone). The resulting precipitate can be separated from the precipitating agents through dialysis after redissolution in water or another solvent.

The soluble fraction, which contains the proteins, carbohydrates and possibly lipids, is collected after the centrifugation and filtration steps. This crude solution is then hydrolyzed under mild conditions in order to generate soluble peptides. Hydrolysis is defined as a chemical reaction involving the cleavage of a molecule by water, and this reaction can take place in a neutral, acidic or basic medium. According to the invention, hydrolysis is carried out chemically and/or advantageously by means of proteolytic enzymes, in which case examples include endoproteases of plant origin (papain, bromelain, ficin).

For the same reasons as stated above, that is to say for removing polyphenolic substances, an amount of polyvinyl polypyrrolidone may be added to the reaction mixture at this stage of the mild hydrolysis. The extract obtained may be further purified in order to select low molecular weight peptide compounds. Fractionation can advantageously be carried out by ultrafiltration and/or by means of a method of the chromatographic type.

This is followed by a dilution phase in water or any mixture of water-containing solvents. Thus, the active agent according to the invention is advantageously dissolved in one or more physiologically acceptable solvents, such as water, glycerol, ethanol, propanediol, butylene glycol, dipropylene glycol, ethoxylated or propoxylated diglycols, cyclic polyols or any mixture of these solvents. The diluted active agent is then sterilized by ultrafiltration.

After this dilution, a peptide extract is obtained, which is characterized by a dry weight of 2 to 5 g/kg, a concentration of peptide compounds of 1 to 10 g/l, preferably from 1.5 to 3.5 g/l, a sugar concentration of 0.05 to 1 g/l, preferably from 0.1 to 0.3 g/l and a polyphenol concentration of less than 1% by dry weight. The solvents used are physiologically acceptable and conventionally used by the skilled person, and are selected from glycerol, ethanol, propanediol, butylene glycol, dipropylene glycol, ethoxylated or propoxylated diglycols, cyclic polyols or any mixture of these solvents.

The extract obtained according to the invention is analyzed qualitatively and quantitatively, using conventional techniques well known to those skilled in the art, for its physicochemical characteristics and its protein- and peptide-based compound content.

The obtained extract is composed of peptides having a molecular weight of less than 5 kDa and is characterized by a sugar concentration of less than 15% and a polyphenol concentration of less than 1% by dry weight.

The second object of the present invention is to provide a composition comprising, in a physiologically acceptable medium, as an active promoter of aquaporin expression, the carob bean peptide extract according to the invention at a concentration ranging between 0.0001% and 20% of the total weight of the composition, preferably at a concentration ranging between 0.05% and 5% of the total weight of the composition.

The active agent can be encapsulated or incorporated in a cosmetic or pharmaceutical carrier such as liposomes or any other microcapsule used in the cosmetic field or adsorbed onto powdered organic polymers, mineral substrates such as talcs and bentonites.

These compositions can be provided, in particular, in the form of an aqueous, hydroalcoholic or oily solution; an oil-in-water or water-in-oil emulsion or multiple emulsions; and may also be provided in the form of creams, suspensions, as well as powders, suitable for application to the skin, mucous membranes, lips and/or keratinous appendages. These compositions may be more or less fluid and take the form of a cream, lotion, milk, serum, ointment, gel, paste or mousse. They can also take a solid form, such as a stick, or be applied to the skin in aerosol form. They can be used as a skin care product and/or as make-up for the skin.

These compositions further comprise any additive commonly used in the intended field of application as well as adjuvants necessary for their formulation, such as solvents, thickeners, diluents, antioxidants, colorants, sunscreens, self-tanning agents, pigments, fillers, preservatives, perfumes, odor absorbers, cosmetic or pharmaceutical active ingredients, essential oils, vitamins, essential fatty acids, surfactants, film-forming polymers, etc.

In all cases, those skilled in the art will ensure that these adjuvants and their proportions are chosen so as not to impair the advantageous properties of the composition according to the invention. These adjuvants can, for example, correspond to between 0.01 and 20% of the total weight of the composition. When the composition of the invention is an emulsion, the fatty phase can represent from 5 to 80% by weight and preferably from 5 to 50% by weight of the total weight of the composition. Emulsifiers and co-emulsifiers used in the composition will be selected from those conventionally used in the field. For example, they can be used in a proportion ranging from 0.3 to 30% by weight, based on the total weight of the composition.

The composition usable according to the invention may be applied by any suitable route including an oral, parenteral or topical external route, and the formulation of the compositions will be adapted by the skilled person.

Advantageously, the compositions according to the invention are provided in a form suitable for topical application. These compositions must therefore contain a physiologically acceptable medium, i.e. compatible with the skin and keratinous appendages, and cover all cosmetic and dermatological forms.

The invention is obviously intended to mammals in general, and particularly to humans.

It is understood that the active agent of the invention may be used alone or in combination with other active agents. Thus, the compositions according to the invention also contain various active agents promoting the action of said peptide extract. For example, the composition of the invention may associate another active agent moisturizer such as glycerol. This association is particularly beneficial and offers optimal hydration efficiency, when compared to the use of glycerol alone.

The following ingredients can also be mentioned, without limitation: healing, anti-aging, anti-wrinkle, soothing agents, free-radical scavengers, anti-UV agents, agents that stimulate dermal macromolecule synthesis or energy metabolism, hydrating, antibacterial, antifungal, anti-inflammatory, anesthetic agents, agents that modulate differentiation, pigmentation or skin depigmentation, agents that stimulate nail or hair growth.

Preferably, an agent with an anti-wrinkle activity will be used, such as a free-radical scavenger or antioxidant, or an agent that stimulates dermal macromolecule synthesis, an agent that stimulates energy metabolism, or a metalloproteinase inhibitor.

For example, other active ingredients having an anti-oxidant or free-radical scavenging action can be added, which are selected from vitamin C, vitamin E, coenzyme Q10 and polyphenol extracts of plants, namely retinoids.

The composition of the invention can also combine other active ingredients with the active ingredient according to the invention, which stimulate dermal macromolecule synthesis (laminin, fibronectin, collagen), such as for example, the collagen peptide marketed as "Collaxyl®" by Vincience.

A third object of the present invention is to provide a pharmaceutical composition comprising, in a physiologically acceptable medium, the peptide extract according to the invention used as a medication. The pharmaceutical composition according to the invention will allow aquaporin activity to be regulated and/or stimulated. The pharmaceutical composition may be intended for preventing or treating pathological dryness of the skin or mucous membranes.

The pharmaceutical composition may also be intended to prevent or treat pathologies caused by aquaporin dysfunction in the skin and mucous membranes, such as eczema, xerosis, atopic dermatitis, or oral, ocular or vaginal dryness.

According to this embodiment of the invention, the compositions are adapted to oral administration for pharmaceutical use. Thus, the compositions can take the form of tablets, capsules, hard gelatin capsules, chewing gums, powders edible as such or to be mixed extemporaneously with a liquid, syrup, gels, and any other form known to those skilled in the art. These compositions also comprise any additive commonly used in the intended field of application as well as the adjuvants required for their formulation, such as solvents, thickeners, diluents, antioxidants, preservatives, other pharmaceutical active ingredients, essential oils, vitamins, essential fatty acids, etc.

A fourth object of the present invention is the cosmetic use of the carob bean peptide extract (*Ceratonia siliqua* L.) according to the invention, as an active moisturizing, barrier function-improving, and regenerating agent.

Thus according to this object of the present invention, the carob bean peptide extract is used in a cosmetic composition for improving skin hydration and preventing or controlling dryness of the skin and mucous membranes.

According to this same object of the present invention, the carob bean peptide extract is used in a cosmetic composition for improving the barrier function of the epidermis.

According to this embodiment of the present invention, the carob bean peptide extract can also be used in a cosmetic composition for protecting the skin and mucous membranes against all types of external aggression.

By "external aggression" are meant aggressions that can be generated by the environment. These can include pollution, ultraviolet radiation, or also irritating products such as surfactants, preservatives or perfumes. By pollution is meant both "outdoor" pollution, for example due to diesel particles, ozone and heavy metals, and "indoor" pollution which may be due in particular to solvent emissions from paints, adhesives, wallpapers (such as toluene, styrene, xylene or benzaldehyde), or even cigarette smoke. Dryness of the atmosphere is also a major cause of skin dryness.

The carob bean peptide extract can thus be used as an active agent in a cosmetic composition for preventing damage caused to the skin by sun exposure or a desiccating environment.

Aggression suffered by the skin and keratinous appendages may also be due to an electrochemical gradient imbalance across the cell membrane, which can lead to significant variations in the osmotic pressure, and this can result in osmotic stress and therefore to cell lysis.

However, the inventors have demonstrated the surprising fact that the active agent according to the invention protects these cells against such osmotic shocks.

Skin may also be damaged by treatments such as shaving. Advantageously, an object of the present invention relates to the use, in a cosmetic composition, of an active agent as described hereinabove, wherein the active agent or the composition containing the same, is intended to prevent or treat damage caused to the skin by shaving.

According to this embodiment of the present invention, the carob bean peptide extract can also be used in a cosmetic composition for stimulating skin regeneration.

According to this embodiment of the present invention, the carob bean peptide extract can also be used in a cosmetic composition for preventively and/or curatively combatting manifestations of skin aging and, more specifically, for combatting and/or preventing photo-induced aging (photo-aging). By cutaneous manifestations of aging, is meant any change in the external appearance of the skin or keratinous appendages due to aging, such as wrinkles and fine lines, withered skin, soft skin, thinned skin, lack of elasticity and/or skin tone, dull and faded skin or skin pigmentation spots, hair bleaching or stains on the nails, but also any internal modification of the skin that does not systematically translate to a modified external appearance such as, for example, any internal degradation of the skin following exposure to ultraviolet (UV). The active agent according to the invention or the composition containing the same, can, in particular, combat the loss of elasticity and firmness of the skin.

The present invention also relates to a cosmetic treatment method for improving skin appearance and preventing or combatting dryness of the skin and mucous membranes, which comprises applying a composition according to the invention to the areas to be treated.

The present invention further relates to a cosmetic treatment method for preventing and/or combatting signs of skin aging and/or photo-aging, which comprises applying a composition according to the invention to the areas to be treated.

Particular embodiments of this cosmetic treatment method will also be apparent from the foregoing description. Other advantages and features of the present invention will become apparent from the examples given by way of non-limiting illustration.

EXAMPLE 1

Preparation of a Peptide Extract of Carob (*Ceratonia siliqua* L.)

Carob beans (*Ceratonia siliqua* L.) in powder form are dissolved in 70 volumes of water and the pH is adjusted to a value between 4.5 and 5.5.

To remove insoluble sugars, hydrolysis is performed by means of a cellulase. For this purpose, 2% Celluclast CL® (Novozym) and 2% Polyclar® 10 (polyvinyl pyrrolidone—PVPP—insoluble) are added to the reaction medium. The reaction mixture is then heated for two hours at 50° C. and then deactivated for one hour at 80° C. The carbohydrate-rich filtrate is removed by means of a filtration step in order to retain the solid residue only.

The latter is characterized by a protein content between 45 and 50% and a sugar content of between 20 and 30%.

The dry residue thus obtained is dissolved in 100 volumes of water in the presence of 2% of Polyclar® 10. The mixture is adjusted to a pH between 8.0 and 8.5 with a 2M aqueous sodium hydroxide solution.

In order to improve protein extraction, a first hydrolysis is carried out using 2% Alcalase® (Novozym). Hydrolysis is achieved after 2 hours, under stirring at 55° C. Inactivation of the enzyme is carried out by heating the solution to 80° C. for 2 hours. After deactivation, the reaction mixture is filtered and the filtrate is collected. The latter consists in the intermediate carob bean protein extract.

At this stage of the preparation, the peptide and protein compounds of this filtrate are characterized by means of polyacrylamide gel electrophoresis (NuPAGE® Bis-Tris Precast gels, Invitrogen). For this purpose, the filtrate is heated at 70° C. for 10 minutes under reducing and denaturing conditions in a NuPAGE® LDS sample preparation buffer. An antioxidant NuPAGE® solution is added to the inner vessel (cathode) to prevent the reduced proteins from being re-oxidized during electrophoresis. Protein migration is performed in a NuPAGE® MES migration buffer in the presence of a molecular weight standard (SeeBlue Plus2). Protein staining is performed using Coomassie® Blue R-250. The obtained protein profile shows that the molecular weights of the filtrate's peptide and protein compounds are in the range between 50 and 10 kDa.

The intermediate carob bean protein extract is then dissolved in 100 volumes of water in the presence of 2% Polyclar® 10. The mixture is adjusted to between 4 and 5 pH units using an aqueous solution of 1 M hydrochloric acid.

A protein hydrolysis step is then carried out using an endoprotease. For this purpose, 2%-bromelain is added to the reaction medium. Hydrolysis is achieved after stirring for 2 hours at 50° C. Inactivation of the enzyme is carried out by heating the solution to 80° C. for 2 hours.

Purification of the thus obtained extract is followed by successive filtrations using Seitz-Orion filter-plates with decreasing porosity (down to 0.2 μm) in order to obtain a bright and clear solution. After this series of filtration steps, the carob bean extract is characterized by a dry weight of 20-25 g/kg, a protein content of 10-15 g/l, a sugar level of 5-6 g/l, an amino acid content of 1-2 g/l and a total polyphenol content of 0.5-1 g/l. The proteins are assayed by means of a specific colorimetric method (Lowry's method).

The protein profile of this extract is analyzed by gel electrophoresis. Under the same conditions as described above, two large protein families are observed: the first, small family, corresponds to proteins having a molecular weight of between 25 and 20 kDa and the second, much greater family, corresponds to proteins with a molecular weight of less than 5 kDa.

This extract is then purified by eliminating the protein whose molecular weight is greater than 5 kDa by tangential flow filtration steps. For that purpose, the carob bean extract is pumped under pressure through a Pellicon® holder equipped with 30-kDa Pellicon® 2 Biomax cassettes. The 1st filtrate is recovered and then re-filtered through another 5-kDa Pellicon® 2 Biomax cassette.

When purification is complete, a yellow-orange, bright and clear carob bean extract is obtained. It is characterized by a dry weight of 8-9 g/kg, a protein content of 6-7 g/l, a sugar content of between 0.3 and 0.5 g/l and a total polyphenol content of less than 0.1 g/l.

A dilution phase is then carried out in a water-glycerol mixture in order to obtain a peptide extract characterized by a dry weight of 2 to 5 g/kg, a peptide compound concentration of 1.5 to 3.5 g/l, a sugar concentration of 0.1 to 0.3 g/l (i.e. less than 15%) and a polyphenol concentration of less than 1%.

This purified and diluted extract corresponds to the carob bean peptide extract of the invention. It is characterized by the fact that the peptide compounds are peptides with molecular weights of less than 5 kDa, and that the polyphenol content is less than 1%.

This solution is then analyzed by high-pressure liquid chromatography using a HP 1100 apparatus driven by the ChemStation software. The column used during the elution of the carob extract is a Nucleosil® MPN 300-5 C4 (125×4 nm). This column can chromatograph proteins having molecular weights in the range from 0.2 to 25 kDa (with a suitable gradient solvent). Under these chromatographic conditions, several peptide fractions were isolated. These various fractions were analyzed by mass spectrometry to identify their molecular peaks. The amino acid composition has also been determined. It is obtained after acid hydrolysis and identification through high-pressure liquid chromatography using PICT (phenylisothiocyanate) pre-bypass.

EXAMPLE 2

Assessment of the Protective Effect of the Active Agent According to Example 1 with Respect to an Osmotic Shock The purpose of this study is to determine the protective effect of the active agent according to Example 1 with respect to normal human keratinocytes subjected to a sorbitol-induced osmotic shock. Assessment of the cellular state is then performed by means of a MTT viability test.

Protocol:

Normal human keratinocytes in culture were placed in the presence of 0.5%, 1% and 3% of the active agent according to Example 1, 24 hours before and during the osmotic shock. The hypertonic culture conditions are achieved by adding 250 mM sorbitol to the culture medium for 24 hours. Untreated controls are made.

Cell viability tests were then conducted by the MTT technique. The MTT agent (3-[4,5-dimethylthiazol-2-yl]-2,5-diphenyltetrazolium bromide) is used to assess cell viability. The keratinocytes are incubated in a solution containing 0.1 mg/ml MTT (3-[4,5-dimethylthiazol-2-yl]-2,5-diphenyltetrazolium bromide). This compound is absorbed by living cells and then metabolized by mitochondrial enzymes (succinate dehydrogenase) into a blue-violet compound, formazan, which is in the form of violet crystals insoluble in aqueous media.

The formazan crystals are dissolved in DMSO, and provide an optical density (OD) proportional to the number of living cells in the sample. Optical density measurements were then performed for each sample studied (with the OD being read at 540 nm). The OD is then directly proportional to the enzyme activity and to the number of living cells.

Results:

The results obtained show a dose-dependent increase in viability of the cells subjected to an osmotic shock when the cells are treated with the active agent according to Example 1, in comparison with untreated cells. The increased viability is greater than 10% when the cells are treated with the active agent according to Example 1 at 3%.

Conclusions:

The active agent according to Example 1 effectively protects normal human keratinocytes subjected to osmotic shock.

EXAMPLE 3

Assessment of the Protective Effect of the Active Agent According to Example 1 with Respect to Induced Skin Dehydration The purpose of this study is to determine the protective effect of the active agent according to Example 1, with respect to ex vivo epidermis cultures subjected to an induced skin dehydration stress.

Protocol:

Biopsies of human skin are stripped of their stratum corneum by stripping, by means of an adhesive tape (tape stripping) and then maintained in ex vivo culture, treated with a 1% solution of the active agent according to Example 1, for 24 hours. The absence of stratum corneum induced severe dehydration. Hematoxylin-eosin (H&E) histological sections and staining allow the quality of the skin structure to be assessed.

Results:

The observation of skin sections show a marked decrease in the signs of cellular stress and better preservation of cutaneous structures in biopsies of skin treated with the active agent according to Example 1, compared with untreated skin biopsies. On the other hand, the appearance of the keratinocytes from the basal layer shows a regenerating effect of the active agent according to Example 1.

Conclusions:

The active agent according to Example 1 effectively protects the skin from dehydration-induced stress. Moreover, the active agent according to Example 1 allows the epidermis to be regenerated.

EXAMPLE 4

Demonstration of the Promoting Effect of the Active Agent According to Example 1 on Claudin and Keratin K10 Expression The purpose of this study is to determine the influence of the active agent according to Example 1 on claudin and keratin K10 expression. Claudins are the main transmembrane proteins of intercellular adhesion structures known as tight-junctions, which play a role in cell communication and epidermal cohesion.

Keratin K10 is a specific keratin of the differentiated epidermal layers (stratum granulosum) and is involved in the bather function of skin. The amount of protein was assessed by immunofluorescence on sections of human skin.

Protocol:

Human skin samples were cultured at the air/liquid interface. A 1% solution of the active agent according to Example 1 is topically applied, and the samples are then incubated for 24 hours.

These skin samples are then fixed with formaldehyde and thereafter embedded in paraffin. 2 to 3-µm sections are then obtained. Immunolabeling is carried out after various steps of washing and incubating these sections.

Immunolabeling of Claudin-1 is achieved by means of a claudin-1-specific antibody (claudin-1 antibodies: rabbit polyclonal, ref: AM15098, Abcam, $1/200^{th}$ dilution), followed by a secondary antibody, coupled with a fluorescent marker (Alexa Fluor 488 donkey anti-rabbit IgG, A21206, Molecular Probes, $1/1000^{th}$).

Immunolabeling of Keratin 10 is achieved using a keratin 10-specific antibody (K10 antibodies: mouse monoclonal ref: LHP1, Novocastra, $1/50^{th}$ dilution), followed by a secondary antibody, coupled with a fluorescent label (Alexa Fluor 488 donkey anti-mouse IgG, A21202, Molecular Probes, $1/1000^{th}$).

The skin sections are then examined with an Epi-fluorescence microscope (Nikon Eclipse E600 microscope).

Results:

Microscopic observations show a stronger fluorescence in skin treated with the 1% active agent according to Example 1, in particular the upper layers of the epidermis for both claudin-1 protein and keratin K10.

Conclusions:

The active agent according to Example 1 strongly stimulates claudin expression, in particular in the upper layers of the epidermis. Similarly, the active agent according to Example 1 strongly stimulates the expression of keratin K10, and more generally the skin barrier functions.

EXAMPLE 5

Demonstration of the Stimulating Effect of the Active Agent According to Example 1 on Aquaporin Expression The purpose of this study is to determine the influence of the active agent according to Example 1 on the expression of aquaporin 3 in ex vivo skin samples.

Protocol:

Human skin samples are cultured at the air/liquid interface. A 1% solution of the active agent according to Example 1 is topically applied, and the samples are then incubated for 24 hours or 48 hours.

These skin samples are then fixed with formaldehyde and thereafter embedded in paraffin. 2 to 3-µm sections are then obtained. Immunolabeling is carried out after various steps of washing and incubating of these sections. The immunolabeling is performed using an aquaporin 3-specific polyclonal antibody (Anti-Aquaporin 3 (C-18): goat polyclonal, sc-9885, Santa Cruz, $1/100^{th}$ dilution), followed by a secondary antibody, coupled with a fluorescent marker (Alexa-fluor 488 donkey anti-goat IgG, Molecular Probes, $1/1000^{th}$ dilution). The skin sections are then examined with an Epi-fluorescence microscope (Nikon Eclipse E600 microscope).

Microscopic observations show a stronger fluorescence in skin treated with the 1% active agent according to Example 1, in particular in the upper layers of the epidermis compared with the untreated control.

Conclusions:

The active agent according to Example 1 stimulates aquaporin 3 expression, in particular in the upper layers of the epidermis.

EXAMPLE 6

Demonstration of the Effect of the Active Agent According to Example 1 on the Morphology of the Adult Human Epidermis The purpose of this study is to analyze the morphology of the adult human epidermis in order to determine the effect of the active agent according to Example 1 on the quality of the skin structures.

Protocol:

Biopsies of human skin are cultured at the air/liquid interface and treated topically with a 1% or 3% solution of the active agent according to Example 1, for 24 hours. The skin biopsies are then embedded in paraffin and 3 µm-thick histological sections are made. The sections are deposited on Superfrost Plus slides (Menzel Gläser, Thermo Scientific) and then deparaffinized in xylene and rehydrated in a series of alcohol-water solutions. The sections are then stained with 50% hematoxylin for 3 minutes, rinsed, and then stained with 60% eosin for 3 minutes and rinsed with water. The sections are then dehydrated, fitted in a Eukitt apparatus, and examined by optical microscopy.

Results:

The histological sections of skin treated with the active agent show that the stratum corneum is thicker and more cohesive. A greater density of the basal layer cells, which appear better oriented along the vertical axis and more homogeneous, can also be seen.

Conclusions:

The active agent according to Example 1 improves the morphology of the epidermis as a whole.

EXAMPLE 6

Preparation of Compositions

1—Day cream

| Trade Names | INCI Names | wt % |
|---|---|---|
| PHASE A | | |
| MONTANOV 68 | Cetearyl Alcohol (and) Cetearyl Glucoside | 5.00 |
| JOJOBA OIL | *Simmondsia Chinensis* (Jojoba) Seed Oil | 3.00 |
| VASELINE OIL | Paraffinum Liquidum (Mineral Oil) | 2.00 |
| SQUALANE | Squalane | 3.00 |
| CERAPHYL 368 | Ethylhexyl palmitate | 4.00 |
| CERAPHYL 41 | C12-C15 Alkyl Lactate | 3.00 |
| RAPITHIX A-60 | Sodium polyacrylate (and) Hydrogenated Polydecene (and) Trideceth-6 | 0.30 |
| PHASE B | | |
| GLYCERIN | Glycerin | 5.00 |
| ALLANTOIN | Allantoin | 0.10 |
| DEMINERALIZED WATER | Aqua (Water) | qs 100 |
| PHASE C | | |
| ROKONSAL MEP | Phenoxyethanol (and) Methylparaben (and) Ethylparaben (and) Propylparaben | 0.50 |
| PHASE D | | |
| ACTIVE AGENT OF EXAMPLE 1 | | 5% |
| PHASE E | | |
| FRAGRANCE | Perfume (Fragrance) | qs |

Operating Mode:

Weigh the ingredients of the fat phase and heat to 70° C. under stirring. Prepare phase B and heat to 70° C. Emulsify phase A into phase B. Add phase D at about 50° C. under stirring. Add the active agent below 40° C. (Phase D). Perfume and cool to room temperature.

2—Moisture Cream W/O

| Trade Names | INCI Names | wt % |
|---|---|---|
| PHASE A | | |
| ARLACEL P 135 | PEG-30 Dipolyhydroxystearate Isononanoate | 2.00 |
| CERAPHYL 375 | Isostearyl Neopentanoate | 3.00 |
| PANALANE L-14E | Hydrogenated Polyisobutene | 3.00 |
| CERAPHYL ODS | Octyldodecyl Stearate | 9.00 |
| CERAPHYL 368 | Ethylhexyl Palmitate | 3.00 |
| PHASE B | | |
| DEMINERALIZED WATER | Aqua (Water) | qs 100 |
| ATLAS G-2330 | Sorbeth-30 | 4.00 |
| 7 H2O MAGNESIUM SULFATE | Magnesium Sulfate | 0.70 |
| ACTIVE AGENT OF EXAMPLE 1 | | 2% |

-continued

| Trade Names | INCI Names | wt % |
|---|---|---|
| PHASE C | | |
| LIQUAPAR OPTIMA | Phenoxyethanol (and) Methylparaben (and) Isopropylparaben (and) Isobutylparaben (and) Butylparaben | 0.50 |
| PHASE D | | |
| FRAGRANCE | Perfume (Fragrance) | qs |

Operating Mode:

Weigh phase A and heat to 75° C. under stirring. Prepare phase B and heat to 75° C. Emulsify phase B into phase A with vigorous mixing using a rotor-stator.

Homogenize for a few minutes. Abruptly cool with a bath of ice water with vigorous stirring. Add phase C at about 50° C. and add the perfume (phase D) at 40° C. Continue cooling to room temperature.

3—Moisturizer Lotion

| Trade Names | INCI Names | wt % |
|---|---|---|
| DEMINERALIZED WATER | Aqua (Water) | qs 100 |
| GLYCERINE | Glycerin | 2.00 |
| PROPYLENE GLYCOL | Propylene Glycol | 2.00 |
| GLUCAM E-10 | Methyl Gluceth-10 | 1.00 |
| NEOSORB | Sorbitol | 5.00 |
| ALLANTOINE | Allantoin | 0.10 |
| ROKONSAL BSB | Benzoic Acid (and) Sorbic Acid (and) Benzyl Alcohol | 0.30 |
| ACTIVE AGENT OF EXAMPLE 1 | | 0.5% |
| Water soluble FRAGRANCE | Perfume (Fragrance) | qs |

Operating Mode:

Incorporate the ingredients one by one into the required amount of water and stir until well dissolved. Readjust the pH to around 5.5 if necessary. Incorporate the active ingredient at the end of the formulating process. Perfume with a water-soluble fragrance under gentle stirring.

The invention claimed is:

1. A cosmetic composition for promoting aquaporin expression comprising: a carob bean peptide extract in a physiologically acceptable medium, wherein the carob bean peptide extract comprises a concentration of peptide compounds, having a molecular weight of less than 5 kDa, of 1.5 to 3.5 g/L, a sugar concentration of 0.1 and 0.3 g/L, and a polyphenol concentration of less than 1% by dry weight of the extract, wherein the carob bean peptide extract comprises between 0.0001% and 20% of the total weight of the composition.

2. The composition according to claim 1, being provided in a form suitable for topical application.

3. The composition according to claim 1 further comprising at least one other active agent chosen from healing, anti-aging, anti-wrinkle, soothing agents, free-radical scavenging or antioxidant, anti-UV, moisturizing, antibacterial, antifungal, anti-inflammatory, anesthetic agents, agents stimulating dermal macromolecule synthesis or energy metabolism, agents modulating skin differentiation, pigmentation or depigmentation, agents stimulating the growth of nails or hair, or inhibitors of metalloproteinase.

4. A cosmetic treatment method for improving skin appearance and preventing and/or combating dryness of the skin and mucous membranes, wherein at a composition as defined in claim 1 is applied topically to the skin or the mucous membranes to be treated.

5. The composition of claim 1, wherein the concentration of the peptide extract is in the range between 0.05% and 5% of the total weight of the composition.

* * * * *